United States Patent
Zur

(10) Patent No.: US 12,236,373 B2
(45) Date of Patent: Feb. 25, 2025

(54) SYSTEM AND METHOD FOR CROP MONITORING AND MANAGEMENT

(71) Applicant: GADOT AGRO LTD., Givat Brenner (IL)

(72) Inventor: Ehud Zur, Karmey Yosef (IL)

(73) Assignee: GADOT AGRO LTD., Kidron (IL)

( * ) Notice: Subject to any disclaimer, the term of this patent is extended or adjusted under 35 U.S.C. 154(b) by 0 days.

(21) Appl. No.: 17/642,215

(22) PCT Filed: Sep. 10, 2020

(86) PCT No.: PCT/IL2020/050987
§ 371 (c)(1),
(2) Date: Mar. 10, 2022

(87) PCT Pub. No.: WO2021/048848
PCT Pub. Date: Mar. 18, 2021

(65) Prior Publication Data
US 2022/0318693 A1    Oct. 6, 2022

Related U.S. Application Data

(60) Provisional application No. 62/898,727, filed on Sep. 11, 2019.

(51) Int. Cl.
*G06Q 10/00*    (2023.01)
*A01G 7/06*    (2006.01)
(Continued)

(52) U.S. Cl.
CPC ............... *G06Q 10/04* (2013.01); *A01G 7/06* (2013.01); *F16M 11/126* (2013.01);
(Continued)

(58) Field of Classification Search
None
See application file for complete search history.

(56) References Cited

U.S. PATENT DOCUMENTS 5,870,689 A * 2/1999 Hale .................... A01B 79/005
                                                    702/5
6,653,971 B1 * 11/2003 Guice .................... G01S 13/88
                                                     342/28
(Continued)

FOREIGN PATENT DOCUMENTS

CN          86103318 A      1/1987
CN         101169627 A      4/2008
(Continued)

OTHER PUBLICATIONS

R Struthers, A Ivanova, L Tits, R Swennen ( . . . —International Journal of . . . , 2015—Elsevier). (Year: 2015).*
(Continued)

*Primary Examiner* — Hafiz A Kassim
(74) *Attorney, Agent, or Firm* — Sughrue Mion, PLLC

(57) ABSTRACT

A crop management system including at least one crop monitoring subsystem including at least one crop sensor assembly for sensing at least one crop growth parameter in a predetermined region, at least one field monitoring subsystem including at least one field sensor assembly for sensing at least one field parameter in the predetermined region, an analysis engine receiving an output from at least one of the at least one crop monitoring subsystem and the at least one field monitoring subsystem and being operative to identify at least one anomaly in at least one of the parameters and an anomaly locator operative to provide an output indication of spatial coordinates of at least one location of the at least one anomaly.

19 Claims, 9 Drawing Sheets

(51) Int. Cl.
*F16M 11/12* (2006.01)
*G01N 33/00* (2006.01)
*G06Q 10/04* (2023.01)
*B64D 1/16* (2006.01)
*B64U 20/40* (2023.01)
*B64U 101/40* (2023.01)
*B64U 101/45* (2023.01)
*B64U 101/60* (2023.01)

(52) U.S. Cl.
CPC ........... *G01N 33/0098* (2013.01); *B64D 1/16* (2013.01); *B64U 20/40* (2023.01); *B64U 2101/40* (2023.01); *B64U 2101/45* (2023.01); *B64U 2101/60* (2023.01)

(56) References Cited

U.S. PATENT DOCUMENTS

| | | | |
|---|---|---|---|
| 10,034,423 | B2 | 7/2018 | Dybro et al. |
| 10,255,670 | B1* | 4/2019 | Wu .................. H04N 7/183 |
| 10,512,212 | B2 | 12/2019 | Koch et al. |
| 10,593,109 | B1* | 3/2020 | Floyd .................. G05D 1/0094 |
| 11,263,707 | B2 | 3/2022 | Perry et al. |
| 2007/0208511 | A1 | 9/2007 | Glenn et al. |
| 2013/0308675 | A1* | 11/2013 | Sneed .................. G01N 33/0098 374/121 |
| 2014/0058881 | A1* | 2/2014 | Rosenbaum .......... G06Q 50/02 705/26.7 |
| 2014/0358486 | A1* | 12/2014 | Osborne .................. A01G 7/00 702/189 |
| 2015/0015697 | A1* | 1/2015 | Redden .................... A01G 7/06 382/110 |
| 2015/0370935 | A1* | 12/2015 | Starr ...................... G06Q 10/06 703/11 |
| 2016/0029558 | A1 | 2/2016 | Dybro et al. |
| 2017/0015416 | A1* | 1/2017 | O'Connor ............ A01B 79/005 |
| 2018/0077852 | A1* | 3/2018 | George .................. A01G 25/16 |
| 2018/0168094 | A1 | 6/2018 | Koch et al. |
| 2018/0325051 | A1* | 11/2018 | De Mello Brandao ...................... G06F 18/24133 |
| 2019/0050948 | A1 | 2/2019 | Perry et al. |
| 2019/0179054 | A1* | 6/2019 | Kleeman ................ G06Q 50/02 |
| 2019/0259108 | A1 | 8/2019 | Bongartz et al. |
| 2020/0337235 | A1* | 10/2020 | Blank .................. A01M 21/043 |

FOREIGN PATENT DOCUMENTS

| | | | | |
|---|---|---|---|---|
| CN | 201869599 | U | 6/2011 | |
| CN | 105050383 | A | 11/2015 | |
| CN | 106305371 | A | 1/2017 | |
| CN | 107711439 | A | 2/2018 | |
| JP | 2004-151092 | A | 5/2004 | |
| JP | 2014-198012 | A | 10/2014 | |
| JP | 2014-215215 | A | 11/2014 | |
| JP | 2015-8699 | A | 1/2015 | |
| JP | 2015-208255 | A | 11/2015 | |
| JP | 2016-123369 | A | 7/2016 | |
| KR | 10-2018-0055604 | A | 5/2018 | |
| WO | WO-2016134341 | A1 * | 8/2016 | ............... G06N 5/04 |
| WO | 2018/073899 | A1 | 4/2018 | |
| WO | 2021/048848 | A2 | 3/2021 | |

OTHER PUBLICATIONS

H Zhu et al. (Development of UAV-based lidar crop height mapping system), 2017—ideals.illinois.edu. (Year: 2017).*
M Ronkainen et al. (Designing a drone based measurement system for outdoor material fields in industrial environment) 2016—oulurepo.oulu.fi. (Year: 2016).*
KO Were et al. (Monitoring spatio-temporal dynamics of land cover changes in Lake Naivasha drainage basin, Kenya) 2008—filetransfer.itc.nl. (Year: 2008).*
A Hawdon, D McJannet et al. (Calibration and correction procedures for cosmic-ray neutron soil moisture probes located across Australia) Water Resources Research, 2014—Wiley Online Library. (Year: 2014).*
U.S. Appl. No. 62/898,727, filed Sep. 11, 2019.
An Invitation to pay additional fees dated Jan. 14, 2021, which issued during the prosecution of Applicant's PCT/IL2020/050987.
An International Preliminary Report on Patentability dated Mar. 15, 2022, which issued during the prosecution of Applicant's PCT/IL2020/050987.
An International Search Report and a Written Opinion both dated Mar. 30, 2021, which issued during the prosecution of Applicant's PCT/IL2020/050987.
An Office Action together with an English summary dated Mar. 3, 2023, which issued during the prosecution of Chinese Patent Application No. 202080062935.6.
An Office Action together with an English summary dated Aug. 31, 2023, which issued during the prosecution of Chinese Patent Application No. 202080062935.6.
Xuezhu, Liu, and Zhang Liangen. "Differences of diurnal changes in canopy temperature of winter wheat under the water stress condition." Acta Agriculturae Universitatis Pekinensis 20.2 (1994): 229-232.—Abstract.
European Search Report dated Aug. 22, 2023 which issued during the prosecution of Applicant's European App No. 20863283.6.
Kusnierek, Krzysztof, and Audun Korsaeth. "Challenges in using an analog uncooled microbolometer thermal camera to measure crop temperature." International Journal of Agricultural and Biological Engineering 7.4 (2014): 60-74.
Lenthe, J-H., E-C. Oerke, and H-W. Dehne. "Digital infrared thermography for monitoring canopy health of wheat." Precision Agriculture 8 (2007): 15-26.
Munir, M. Safdar, Imran Sarwar Bajwa, and Sehrish Munawar Cheema. "An intelligent and secure smart watering system using fuzzy logic and blockchain." Computers & Electrical Engineering 77 (2019): 109-119.
Communication dated Aug. 27, 2024 issued by the Japanese Patent Office in application No. 2022-515546.

* cited by examiner

SYSTEM AND METHOD FOR CROP MONITORING AND MANAGEMENT

RELATED APPLICATIONS

This patent is a National Entry Phase of PCT Patent Application PCT/IL2020/050987 filed Sep. 10, 2020, which claims priority to U.S. application 62/898,727 filed Sep. 11, 2019. All references cited in this section are incorporated here by reference in their entirety.

FIELD OF THE INVENTION

The present invention relates to automated crop growth management, monitoring, amelioration and assessment systems and methodologies.

BACKGROUND OF THE INVENTION

Various systems and methodologies are known for crop growth management, monitoring, amelioration and assessment.

SUMMARY OF THE INVENTION

The present invention seeks to provide improved systems and methodologies for automated crop growth management, monitoring, amelioration and assessment.

There is thus provided in accordance with a preferred embodiment of the present invention a system for crop management including a sensor which is located at a static location during measurement and is capable of sensing at least temperature characteristics of a multiplicity of plants and having a resolution sufficient to distinguish between individual plants or groups of plants and a sensor output processor, receiving an output of the sensor and being operative to provide an output indication of a difference between a rate of change in at least temperature over time of a first specific plant or group of plants and a second specific plant or group of plants spatially adjacent thereto over a time interval of less than one day.

Preferably the sensor output processor is also operative to provide an output indication of a difference between a temperature of the first specific plant or group of plants and a second specific plant or group of plants spatially adjacent thereto.

Preferably, the output indication includes a spatial output location indication specifying the location of the first specific plant or group of plants. The spatial output location indication is preferably expressed in GIS coordinates.

In accordance with a preferred embodiment of the present invention, the sensor comprises a camera which is rotatably mounted on a generally vertical shaft. The generally vertical shaft is preferably a selectably raisable shaft which is mounted on a movable support, which normally does not move during operation of the sensor.

Preferably, the system also includes artificial intelligent analytics operative to ascertain from the output indication a probable cause of the difference.

There is also provided in accordance with a preferred embodiment of the present invention a crop management system including at least one crop monitoring subsystem including at least one crop sensor assembly for sensing at least one crop growth parameter in a predetermined region, at least one field monitoring subsystem including at least one field sensor assembly for sensing at least one field parameter in the predetermined region, an analysis engine receiving an output from at least one of the at least one crop monitoring subsystem and the at least one field monitoring subsystem and being operative to identify at least one anomaly in at least one of the parameters and an anomaly locator operative to provide an output indication of spatial coordinates of at least one location of the at least one anomaly.

Preferably, the crop management system also includes at least one crop protection subsystem for ameliorating the at least one anomaly. Additionally, at least one of the at least one crop monitoring subsystem and the at least one field monitoring subsystem monitors amelioration of the at least one anomaly.

In accordance with a preferred embodiment of the present invention at least one of the at least one crop monitoring subsystem and the at least one field monitoring subsystem includes a sample collector for collecting a sample possibly evidencing the anomaly. Additionally, the crop management system also includes a sample analyzer operative for analyzing the sample and for providing a sample analysis output. Preferably, the analysis engine receives the sample analysis output and employs the analysis output in identifying the at least one anomaly.

In accordance with a preferred embodiment of the present invention at least the analysis engine employs artificial intelligence-based analysis to identify the anomaly.

In accordance with a preferred embodiment of the present invention the crop management system also includes at least one environmental parameter sensing subsystem for sensing at least one environmental parameter in the predetermined region.

Preferably, the at least one crop growth parameter includes at least one of a crop growth influencing parameter and a crop growth indicating parameter.

In accordance with a preferred embodiment of the present invention the at least one environmental parameter includes at least one of ambient temperature, humidity, solar radiation, soil temperature, wind speed, altitude, barometric pressure and rainfall.

Preferably, the at least one crop growth indicating parameter includes at least one of plant size, plant UV spectrum, plant visible spectrum, plant IR spectrum and plant temperature.

In accordance with a preferred embodiment of the present invention the crop management system also includes at least one elevated monitoring platform and at least one crop monitoring payload removably mounted onto at least one of the at least one elevated platform, the crop monitoring payload including at least one of at least one crop monitoring subsystem including at least one crop sensor assembly for sensing at least crop growth parameters in a predetermined region, at least one field monitoring subsystem including at least one field sensor assembly for sensing at least one field parameter in the predetermined region, an analysis engine receiving an output from at least one of the at least one crop monitoring subsystem and the at least one field monitoring subsystem and being operative to identify at least one anomaly in at least one of the parameters and an anomaly locator operative to provide an output indication of spatial coordinates of at least one location of the at least one anomaly.

In accordance with a preferred embodiment of the present invention the at least one crop monitoring payload includes an azimuthal scanner. Additionally or alternatively, the at least one crop monitoring payload includes both pan and tilt capabilities. Preferably, the at least one crop monitoring payload is operative to monitor crops within a radial distance of 400 meters of the platform.

In accordance with a preferred embodiment of the present invention the at least one crop monitoring payload includes a wireless anomaly output generator operative to generate a wireless anomaly output indication via a wireless network.

In accordance with a preferred embodiment of the present invention the crop management system also includes a drone operative to position the at least one payload on the at least one platform. Additionally, the drone is operative to move the at least one payload between multiple ones of the at least one platform. Additionally or alternatively, the drone is operative to position the at least partially automated anomaly ameliorating subsystem for providing treatment to the crops at the at least one location for ameliorating at least one condition giving rise to the at least one anomaly.

In accordance with a preferred embodiment of the present invention the at least one elevated monitoring platform includes a plurality of mutually spaced elevated monitoring platforms and the at least one payload includes a plurality of payloads.

There is also provided in accordance with another preferred embodiment of the present invention a crop monitoring system including at least one elevated monitoring platform, at least one crop monitoring payload removably mounted onto at least one of the at least one elevated platform, at least one of the at least one crop monitoring payload including a sensor assembly for sensing characteristics of crops growing in a vicinity of the payload, an analysis engine receiving an output from the sensor assembly and operative to identify at least one anomaly in the characteristics of the crops and an anomaly locator operative to provide an output indication of spatial coordinates of at least one location of the at least one anomaly.

In accordance with a preferred embodiment of the present invention the crop monitoring system also includes an at least partially automated anomaly ameliorating subsystem for providing treatment to the crops at the at least one location for ameliorating at least one condition giving rise to the at least one anomaly.

In accordance with a preferred embodiment of the present invention the at least one crop monitoring payload includes an azimuthal scanner. Additionally, the at least one crop monitoring payload includes both pan and tilt capabilities.

Preferably, the at least one crop monitoring payload is operative to monitor crops within a radial distance of 400 meters of the platform.

In accordance with a preferred embodiment of the present invention the at least one crop monitoring payload includes a wireless anomaly output generator operative to generate a wireless anomaly output indication via a wireless network.

Preferably, the crop monitoring system also includes a drone operative to position the at least one payload on the at least one platform. Additionally, the drone is operative to move the at least one payload between multiple ones of the at least one platform.

In accordance with a preferred embodiment of the present invention the drone is operative to position the at least partially automated anomaly ameliorating subsystem for providing treatment to the crops at the at least one location for ameliorating at least one condition giving rise to the at least one anomaly. Additionally, the drone receives the spatial coordinates of the at least one location from the anomaly locator.

In accordance with a preferred embodiment of the present invention the at least one elevated monitoring platform includes a plurality of mutually spaced elevated monitoring platforms and the at least one payload includes a plurality of payloads. Additionally, the plurality of payloads includes a plurality of different crop-specific payloads. Additionally or alternatively, the crop monitoring system also includes a drone which operates in association with plural ones of the plurality of payloads.

In accordance with a preferred embodiment of the present invention the at least one elevated monitoring platform is stationary during operation thereof. Additionally, the payload is in a fixed location during operation thereof.

Preferably, the sensor assembly includes a plant stress sensor and the at least one anomaly is a plant stress anomaly. Additionally or alternatively, the sensor assembly includes a thermal sensor and the at least one anomaly is a thermal anomaly. Alternatively or additionally, the sensor assembly includes an optical sensor and the at least one anomaly is a visually sensible anomaly.

In accordance with a preferred embodiment of the present invention the crop monitoring system also includes an image transmitter for transmitting images of the crops exhibiting the anomaly.

Preferably, the crop monitoring system also includes a database storing at least anomaly and anomaly location data.

In accordance with a preferred embodiment of the present invention the analysis engine employs an algorithm which employs multiple environmental and plant growth parameters. Additionally or alternatively, the analysis engine employs an algorithm which employs multiple plant growth parameters and field parameters. Additionally, the algorithm also employs a sensed thermal parameter received from the sensor assembly. Preferably, the algorithm compares a sensed thermal parameter with an average thermal parameter received from multiple sensor assemblies over a predetermined time period.

There is additionally provided in accordance with a preferred embodiment of the present invention a method for crop management including providing a sensor at a static location during measurement for sensing at least temperature characteristics of a multiplicity of plants and having a resolution of individual plants or groups of plants and receiving an output of the sensor and providing an output indication of a difference between a rate of change in at least temperature over time of a first specific plant or group of plants and a second specific plant or group of plants over a time interval of less than one day.

Preferably the method includes providing an output indication of a difference between a temperature of the first specific plant or group of plants and the second specific plant or group of plants spatially adjacent thereto.

Preferably the method additionally includes specifying the location of the specific plant or group of plants, preferably expressed in GIS coordinates.

Preferably the sensor is mounted onto a selectably raisable generally vertical shaft which normally does not move during operation of the sensor.

Preferably the method includes one or more of ascertaining a probable cause of the difference from the output indication, associating the difference with a plant growth anomaly and recommending amelioration of the plant growth anomaly.

Preferably the method also includes associating multiple differences at multiple locations with a plant growth anomaly.

There is further provided in accordance with yet another preferred embodiment of the present invention a crop management method including sensing at least one crop growth parameter in a predetermined region and providing at least one crop growth parameter output, sensing at least one field parameter in the predetermined region and providing at least one field parameter output, receiving at least one of the at least one crop growth parameter output and the at least one field parameter output, identifying at least one anomaly in the at least one of the at least one crop growth parameter output and the at least one field parameter output and providing an output indication of spatial coordinates of at least one location of the at least one anomaly.

Preferably, the crop management method also includes ameliorating the at least one anomaly. Additionally, the crop management method also includes monitoring amelioration of the at least one anomaly. Additionally or alternatively, the crop management method also includes collecting a sample possibly evidencing the anomaly.

In accordance with a preferred embodiment of the present invention the crop management method also includes analyzing the sample and providing a sample analysis output. Additionally, the crop management method also includes receiving the sample analysis output and employing the analysis output in identifying the at least one anomaly.

In accordance with a preferred embodiment of the present invention the crop management method also includes employing artificial intelligence based analysis to identify the anomaly. Additionally or alternatively, the crop management method also includes sensing at least one environmental parameter in the predetermined region.

Preferably, the at least one environmental parameter includes at least one of ambient temperature, humidity, solar radiation, soil temperature, wind speed, altitude, barometric pressure and rainfall.

In accordance with a preferred embodiment of the present invention the at least one crop growth parameter includes at least one of a crop growth influencing parameter and a crop growth indicating parameter. Additionally, the at least one crop growth indicating parameter includes at least one of plant size, plant UV spectrum, plant visible spectrum, plant IR spectrum and plant temperature.

There is yet further provided in accordance with still another preferred embodiment of the present invention a crop monitoring method including providing at least one elevated monitoring platform, removably mounting at least one crop monitoring payload onto at least one of the at least one elevated platform, at least one of the at least one crop monitoring payload including a sensor assembly for sensing characteristics of crops growing in a vicinity of the payload, receiving an output from the sensor assembly, identifying at least one anomaly in the characteristics of the crops and providing an output indication of spatial coordinates of at least one location of the at least one anomaly.

Preferably, the crop monitoring method also includes automatically providing treatment to the crops at the at least one location for ameliorating at least one condition giving rise to the at least one anomaly.

In accordance with a preferred embodiment of the present invention the at least one crop monitoring payload includes an azimuthal scanner. Additionally the at least one crop monitoring payload includes both pan and tilt capabilities.

In accordance with a preferred embodiment of the present invention the crop monitoring method also includes monitoring crops within a radial distance of 400 meters of the platform, utilizing the at least one crop monitoring payload. Additionally or alternatively, the crop monitoring method also includes generating a wireless anomaly output indication via a wireless network.

Preferably, the crop monitoring method also includes positioning the at least one payload on the at least one platform. Additionally, the crop monitoring method also includes moving the at least one payload between multiple ones of the at least one platform.

In accordance with a preferred embodiment of the present invention the crop monitoring method also includes transmitting images of the crops exhibiting the anomaly. Additionally or alternatively, the crop monitoring method also includes storing at least the anomaly and anomaly location data.

BRIEF DESCRIPTION OF THE DRAWINGS

The present invention will be understood and appreciated more fully from the following detailed description, taken in conjunction with the drawings in which.

DETAILED DESCRIPTION OF PREFERRED EMBODIMENTS

Figure 1:
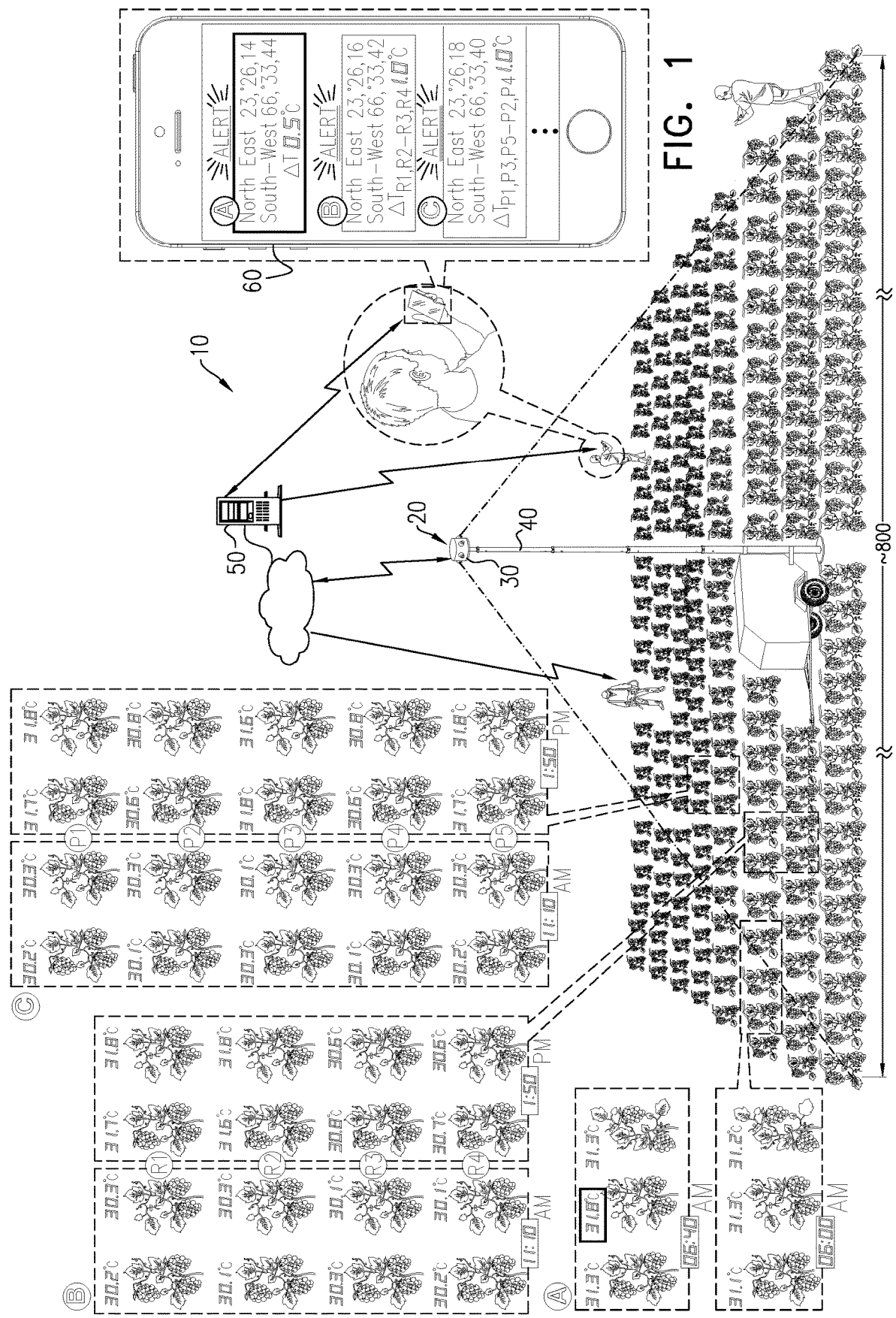
FIG. 1 is a simplified schematic illustration of a crop management system constructed and operative in accordance with a preferred embodiment of the present invention.

Reference is now made to FIG. 1, which is a simplified schematic illustration of a crop management system 10 constructed and operative in accordance with a preferred embodiment of the present invention.

As seen in FIG. 1, the crop management system 10 comprises at least one crop monitoring subsystem comprising at least one crop sensor assembly 20 for sensing at least one crop growth parameter in a predetermined region of growing plants. Preferably, the predetermined region extends up to a radius of 400 meters from the sensor assembly 20. Preferably, the sensor assembly 20 comprises a multi-spectral sensor assembly covering visible and non-visible spectral ranges, preferably extending across the range of 400-1000 nm and 8000-14,000 nm. A preferred embodiment of a sensor assembly 20 is a FLIR 700, commercially available from Flir Systems, Inc. of Wilsonville, OR, USA, which has a thermal deviation resolution of 0.05 degrees Celsius. Another preferred embodiment of a crop sensor assembly 20 is an Altum™ sensor, commercially available from Micasense, Inc of Seattle, WA, USA.

The sensor assembly 20 is preferably mounted onto a raised stabilized platform assembly 30, which preferably provides 360 degree rotation about a vertical axis. A preferred embodiment of a stabilized platform assembly 30 is a CINEMA PRO, commercially available from Gyro-Stabilized Systems LLC of Nevada City, CA, USA.

Stabilized platform assembly 30 is preferably fixedly mounted onto a raisable platform 40 and is maintained at a height of approximately 30 meters above the ground. A preferred embodiment of a raisable platform 40 is a QEAM-HD, commercially available from the Will-Burt Company of Orrville, OH, USA, or a BOSS 100', commercially available from Bossltg, Inc. of Baton Rouge, LA, USA, which are portable telescopic raised platforms, or portable masts, commercially available from Total Mast Solutions Ltd of Leicestershire, UK.

An output of the sensor assembly 20 is preferably supplied, via the cloud or alternatively in any other manner, to an analysis and reporting engine 50, such as a server, which analyzes the output of the sensor assembly and provides an output indication of plant growth anomalies within the predetermined region. An output indication of such anomalies preferably includes an indication of variation in temperature changes over time between adjacent plants, which exceeds a predetermined threshold.

Preferably the output indication is communicated to a hand-held communicator 60, such as a smartphone having installed thereon a suitable app, which enables it to display alerts as to anomalies including an indication of the anomaly and its location, preferably in GIS coordinates. The smartphone may be carried by a grower who is thus enabled to walk directly to the location of the anomaly and examine the plants.

FIG. 1 illustrates three examples of temperature change anomalies that can be reported in near real time:

At A, it is seen that among three adjacent grape vines, one of them has a temperature change of 0.5 degrees Celsius between 6:00 am and 6:40 am, while the two vines adjacent thereto have temperature changes of 0.2 degrees Celsius or less. This may be indicative of a watering problem or an incipient disease. An output indication indicating the anomalous temperature change and the location of the plant in question appears as an alert on the smartphone 60 of the grower.

At B, it is seen that two adjacent rows of grape vines, designated R1 and R2, have a temperature change of 1.5 degrees Celsius between 11:10 am and 1:50 pm, while another two adjacent rows of grape vines, designated R3 and R4, have a temperature change of 0.5 degrees Celsius between 11:10 am and 1:50 pm. This may be indicative of a watering problem or an incipient disease. An output indication indicating the anomalous temperature change and the location of the plant in question appears as an alert on the smartphone 60 of the grower.

At C, it is seen that alternative rows of grape vine, designated P1, P3 and P5, have a temperature change of 1.5 degrees Celsius between 11:10 am and 13:50 pm, while the rows in between them, designated P2 and P4, have a temperature change of 0.5 degrees Celsius between 11:10 am and 13:50 pm. This may be indicative of a watering problem. An output indication indicating the anomalous temperature change and the location of the plant in question appears as an alert on the smartphone 60 of the grower.

In another example, the temperature of rows of corn is monitored vis-á-vis the ambient temperature. It is known that healthy rows of corn have a temperature generally below ambient temperature. Monitoring of a temperature of the rows of corn where the temperature is less than a predetermined threshold, typically 1.0-1.5 degree Celsius, below the ambient temperature may be indicative of a watering problem or an incipient disease. An output indication indicating the anomalous temperature and the location of the plant in question may appear as an alert on the smartphone 60 of the grower.

In a further example, the health of avocado or mango trees is monitored by measuring the temperature of the buds and leaves vis-à-vis the ambient temperature and surrounding trees. Monitoring of a temperature of the buds and leaves where the temperature is less than a predetermined threshold, typically 1.0-1.5 degrees Celsius, below the ambient temperature or where the temperature differs from the surrounding trees by more than a predetermined threshold may be indicative of a watering problem or an incipient disease or an incipient infestation. An output indication indicating the anomalous temperature and the location of the plant in question may appear as an alert on the smartphone 60 of the grower.

It is appreciated that the analysis and reporting engine 50 may include artificial intelligence analytics for suggesting causes of the anomalies and recommending steps for ameliorating same.

For example, as noted above, different temperature pattern changes may be indicative of different problems. Problems may be one or more of system problems, such as dehydration, which may be indicative of a problem in the watering system, environmental problems, such as soil salinity or soil nutrient problems, biological problems, such as air borne or soil borne fungal attacks, and infestation problems.

Figure 2:
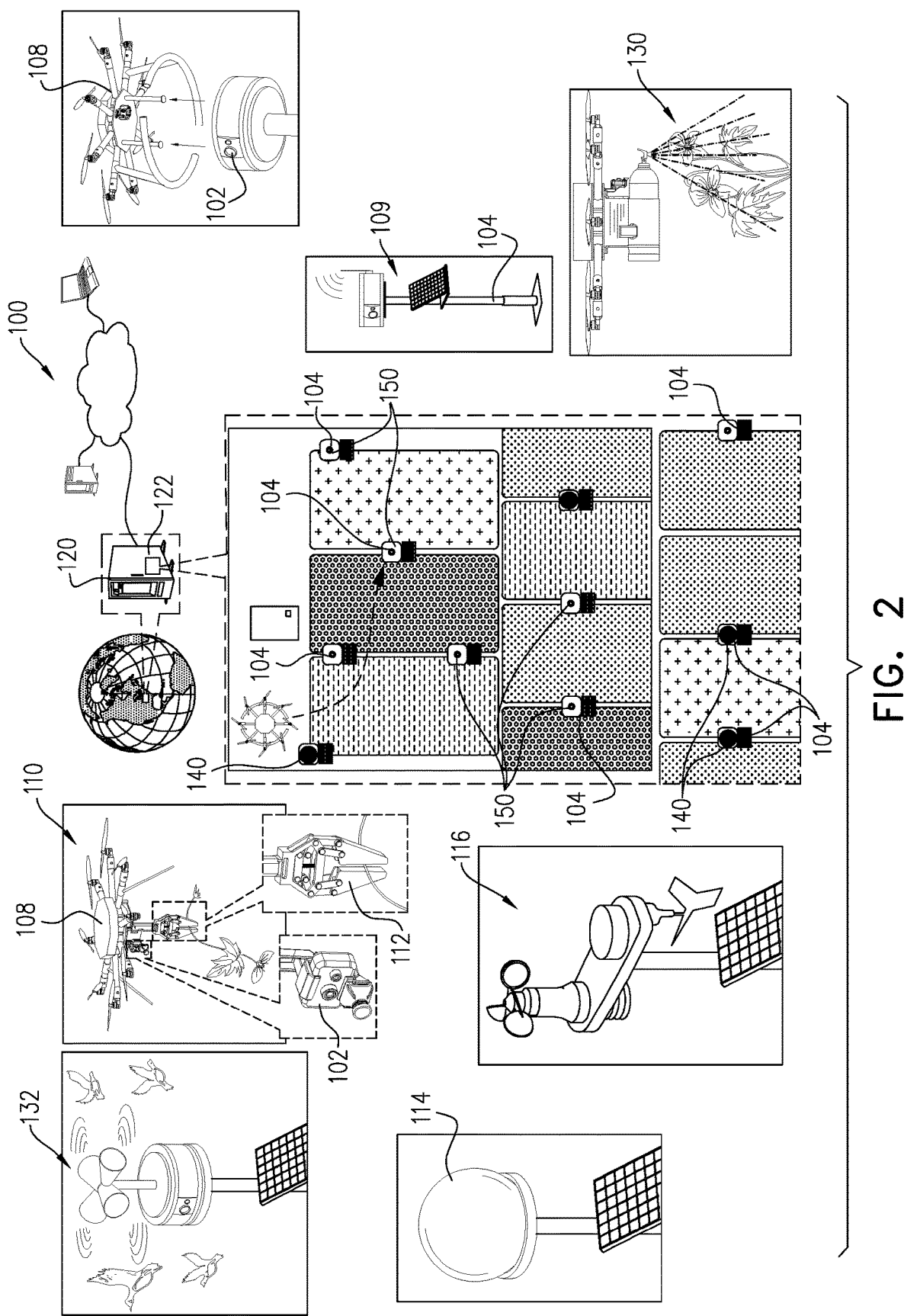
FIG. 2 is a simplified pictorial illustration of a crop management system constructed and operative in accordance with another preferred embodiment of the present invention.

Reference is now made to FIG. 2, which is a simplified schematic illustration of a crop management system 100 constructed and operative in accordance with a preferred embodiment of the present invention.

As seen in FIG. 2, the crop management system 100 comprises at least one crop monitoring subsystem comprising at least one crop sensor assembly 102 for sensing at least one crop growth parameter in a predetermined region. Preferably, the predetermined region extends up to a radius of 400 meters from the sensor assembly 102. Preferably, the sensor assembly 102 comprises a multi-spectral sensor assembly covering visible and non-visible spectral ranges, preferably extending across the range of 400-1000 nm and 8000-14,000 nm. A preferred embodiment of a sensor assembly is a FLIR 700, commercially available from Flir® Systems, Inc. of Wilsonville, OR, USA, which has a thermal deviation resolution of 0.05 degrees Celsius. Another preferred embodiment of a sensor assembly 102 is an Altum™ sensor, commercially available from Micasense®, Inc of Seattle, WA, USA.

The sensor assembly 102 may be movably mounted on a fixed platform 104 during operation by aerial vehicle, such as a drone 108, as indicated at reference numeral 109, or may be mounted on drone 108, as indicated at reference numeral 110. The crop monitoring subsystem may also include a sample collector 112, which may be mounted onto drone 108. FIG. 2 shows a plurality of fixed elevated platforms 104 distributed in a crop growing region.

Crop management system 100 also preferably includes at least one field monitoring subsystem comprising at least one field sensor assembly 114 for sensing at least one field parameter in the predetermined region. One example of a field sensor assembly 114 is a scanning radar assembly, for detection of human or animal intruders, vehicles and rain and for monitoring activity of drones 108, which preferably form part of the crop management system 100. Field sensor assembly 114 may be assembled together with crop sensor assembly 102. Additionally, field sensor assembly 114 and crop sensor assembly 102 may be mounted on the same fixed elevated platforms 104.

Additionally, crop management system 100 preferably includes at least one environmental monitoring subsystem, such as a weather station, as indicated at reference numeral 116, which provides data such as ambient temperature, humidity, wind speed, solar radiation, barometric pressure, as well as soil probes which provide data regarding soil temperature as well as chemical and biological analysis of the soil.

Crop management system 100 preferably also includes an analysis engine 120, receiving an output from at least one of the at least one crop monitoring subsystem and the at least one field monitoring subsystem and being operative to identify at least one anomaly in at least one of the parameters.

Examples of anomalies which can be detected and preferably ameliorated by the crop management system preferably include:
  Crop growth anomalies, including fungal diseases, such as mildew, bacterial diseases, such as fire blight in pears, viral diseases, such as tomato yellow leaf virus (TYLV), insect infestation, such as white fly in tomatoes, and nematodes;
  Field anomalies, such as under irrigation, over irrigation, under fertilization, birds and groundhogs; and
  Environmental anomalies, such as frost, extreme high temperature and extreme high humidity.

The analysis engine 120 is preferably remotely located from the field being managed and preferably resides on a server 122 which may communicate wirelessly with the remainder of the crop management system. It is appreciated that crop sensor assembly 102 and field sensor assembly 114 may also be operative to perform analysis of the parameters sensed and to detect anomalies therein.

It is appreciated that analysis engine 120 may include multiple different methodologies for detecting anomalies, including correlating data received from multiple ones of crop sensor assemblies 102 and field sensor assemblies 114 at a given time, correlating data from a single one of crop sensor assemblies 102 and field sensor assemblies 114 over time and correlating data from multiple ones of crop sensor assemblies 102 and field sensor assemblies 114 over time. It is also appreciate that once analysis engine 120 has determined that an anomaly exists, that analysis engine 120 may employ a variety of analysis tools, including artificial intelligence driven tools, for defining the nature of the anomaly and the appropriate amelioration process. It is further appreciated that the analysis engine 120 may correlate data received from multiple ones of crop sensor assemblies 102 and field sensor assemblies 114 located in the same field or in multiple fields.

Preferably, crop management system 100 further includes an anomaly locator operative to provide an output indication of spatial coordinates of at least one location of the at least one anomaly. The anomaly locator is preferably embodied in one or more encoders associated with at least one of the at least one crop sensor assembly 102 and the at least one field sensor assembly 114 as well as GPS coordinate indicators associated with drones 108.

Preferably, the crop management system 100 also includes various amelioration subsystems for amelioration of anomalies, such as those described above. One example of an amelioration subsystem is a spraying or distribution assembly, such as that indicated at reference numeral 130, which can be mounted on drone 108 and used to deliver fungicides, bactericides, insecticides or other materials for dealing with anomalies, such as distressed crops. Another example of an amelioration subsystem is a bird harassment system, such as that indicated at reference numeral 132.

The embodiment illustrated in FIG. 2 shows a plurality of platforms 104 in a region to be monitored, some of which may have sensor assemblies, such as crop sensor assembly 102 and field sensor assembly 114, mounted thereon and are designated by reference number 140, and some of which do not have sensor assemblies mounted thereon and are designated by reference number 150. As described further hereinbelow with reference to FIG. 4, sensor assemblies may be transportable, such as by drones 108.

Figure 3:
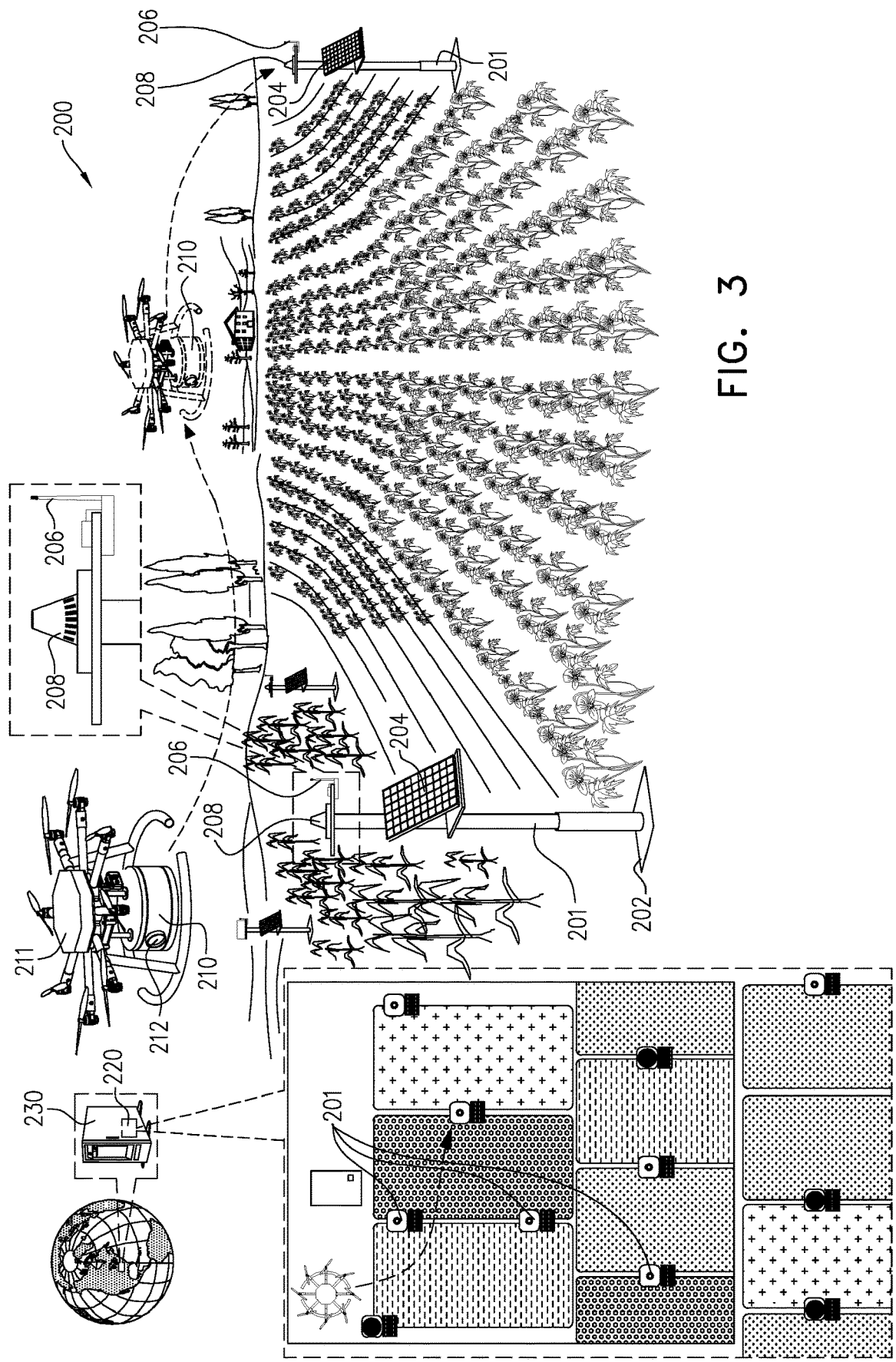
FIG. 3 is a simplified pictorial illustration of a system for monitoring plant growth constructed and operative in accordance with a preferred embodiment of the present invention.

Reference is now made to FIG. 3, which illustrates a system 200 for monitoring plant growth constructed and operative in accordance with a preferred embodiment of the present invention. In accordance with a preferred embodiment, as seen in FIG. 3, the system includes at least one, and preferably multiple, elevated monitoring platforms 201 which are fixed or removably mountable at predetermined or selectable locations in or adjacent to fields in which crops are growing. The crops may be any suitable crops, such as field crops and fruit trees. The platforms 201 may be located between fields in which different crops are growing and enable real time or near real time monitoring of multiple different crops.

Elevated monitoring platforms 201 may be mounted on pre-positioned base elements 202, but do not necessarily require separate base elements. The base elements may include existing posts which are used for lighting, irrigation, power transmission or communications. Platforms 201 preferably each include solar powered, electricity generating panels 204 and wireless communication antennas 206 as well as a payload dock 208. Additionally, each of platforms 201 preferably includes a chargeable battery (not shown) providing backup power.

In accordance with a preferred embodiment of the present invention, monitoring platforms 201 may be removably insertable into base element 202 such that a monitoring platform 201 may be removed from one base element 202 and inserted into a different base element 202, as described further hereinbelow with reference to FIG. 8.

In accordance with a preferred embodiment of the present invention, at least one crop monitoring payload assembly 210 is removably mounted onto each of the elevated platforms 201, preferably by a drone 211, as described hereinbelow with reference to FIG. 4. The crop monitoring payload assembly 210 preferably includes a sensor assembly 212 for sensing characteristics of crops growing in a vicinity of crop monitoring payload assembly 210. The sensor assembly 212 preferably includes at least one sensor and at least one imager, and may additionally include at least one functionality providing assembly. The at least one sensor preferably includes some or all of the following sensors: a temperature sensor, a wind sensor, an IR sensor, an optical sensor, a UV sensor, a humidity sensor, a biological sensor and a chemical sensor. The at least one imager, preferably includes one of the following imagers: a visual imager, a thermal imager and a multispectral imager. The at least one functionality providing assembly is preferably operative to provide one or more of the following functionalities: bird harassment functionality, security functionality, such as radar, relay station functionality and drone battery charging functionality.

In a preferred embodiment, the payload assembly 210 includes focusing and aiming apparatus, similar to that found in crop sensor assembly 102, enabling the sensor assembly 212 to sense characteristics of a given section of a field of growing plants, as well as azimuthal and tilt sensing apparatus, which enables the payload assembly 210 to pinpoint a given area in a field having an anomaly, such as insufficient watering or pest infestation. Preferably, the spatial resolution of the payload assembly is 1 meter×1 meter, more preferably the spatial resolution of the payload assembly is 0.5 meters×0.5 meters, and most preferably, the resolution of the payload assembly is 0.05 meters×0.05 meters.

Preferably, a single payload assembly 210 is able to monitor a crop growing area of 10 hectares. More preferably, the payload assembly 210 is able to monitor a crop growing area of 30 hectares. Most preferably, the payload assembly is able to monitor a crop growing area of 50 hectares.

Preferably, system 200 also includes an analysis engine 220, receiving an output from the sensor assembly 212 and being operative to identify at least one anomaly in characteristics of the growing crops, within the monitoring area of the payload assembly 210. Some examples of anomalies which can be identified using the system 200 include those described hereinabove with reference to FIG. 2.

System 200 also preferably includes an anomaly locator which receives outputs from the analysis engine 220 and provides an output indication of one or more sensed anomalies in the growing crops as well as the spatial coordinates of at least one location of the at least one anomaly. The anomaly locator preferably employs at least one of an encoder and GPS data.

It is appreciated that analysis engine 220 is preferably remotely located from the field being managed and preferably resides on a server 230 which may communicate wirelessly with the remainder of the crop management system. It is appreciated that sensor assembly 212 may also be operative to perform analysis of the parameters sensed and to detect anomalies therein.

Figure 4:
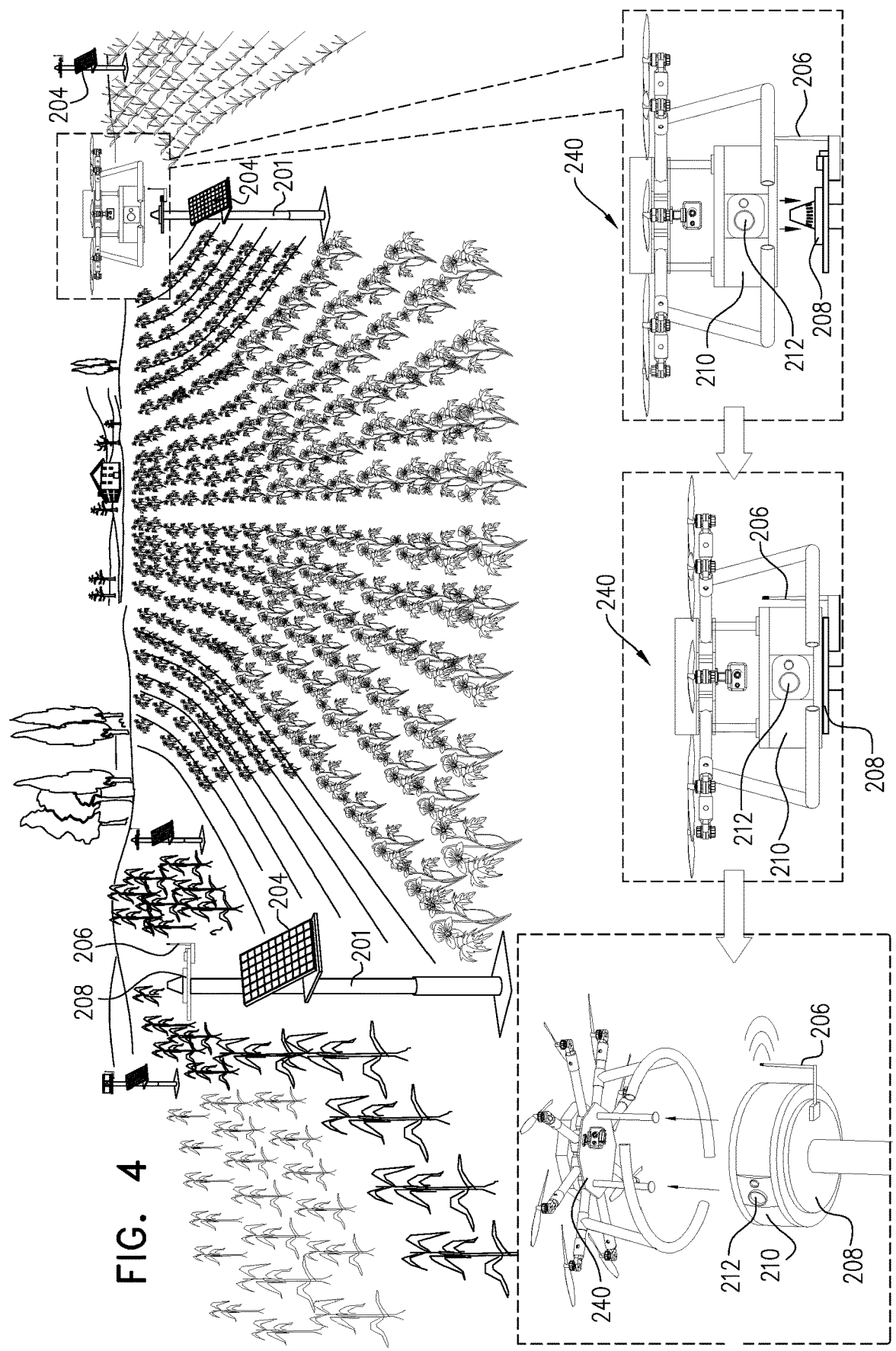
FIG. 4 is a simplified pictorial illustration of one example of docking of a monitoring payload on a pre-positioned elevated support in a system for monitoring plant growth of the type shown in FIG. 3.

Reference is now made to FIG. 4, which is a simplified pictorial illustration of one example of docking of payload 210 on a pre-positioned elevated platform 201 in the system 200 for monitoring plant growth of the type shown in FIG. 3. As seen in FIG. 4, a drone 240 may be employed for transporting a selected one of, preferably, a plurality of, selectable different payload assemblies 210 to a selected one of multiple elevated monitoring platforms 201 and for docking the selected payload assembly 210 onto the selected elevated monitoring platform 201. The docking apparatus has a mechanical interface and an electrical interface. The mechanical interface guides the payload into the required position in such a way that the payload is secured and connected to the electrical connectors forming the electrical interface. The electrical connectors preferably provide power to the system and may also provide connection to a communication interface for communicating with the other components of system 200, including the analysis engine 220 and the anomaly locator. Alternatively, the selected payload assembly 210 includes a communication interface for communicating with the other components of system 200. The payload dock 208 may also provide a housing for payload assembly 210 based on environmental requirements. Payload dock 208 preferably receives power from solar powered, electricity generating panel 204 that is installed on elevated monitoring platform 201. Backup power is preferably provided by the chargeable battery, which preferably is charged during the day time and provides power for night operation.

Figure 5:
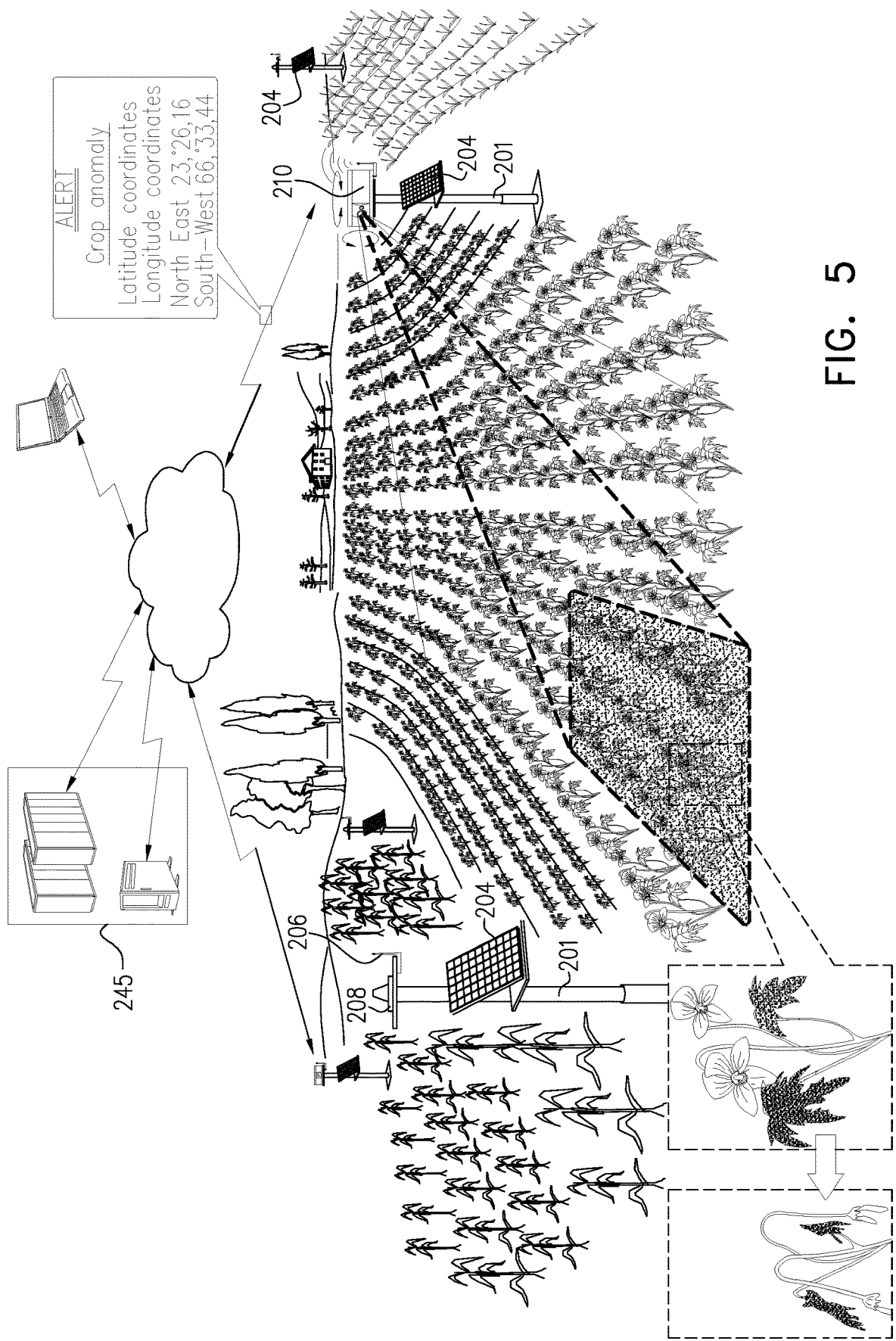
FIG. 5 is a simplified pictorial illustration of one example of operation of the monitoring payload in a system for monitoring plant growth of the type shown in FIGS. 3 and 4.

Reference is now made to FIG. 5, which is a simplified pictorial illustration of an example of operation of payload assembly 210 in system 200 for monitoring plant growth of the type shown in FIGS. 3 and 4. As seen in FIG. 5, the payload assembly 210, preferably scans a region, such as field or a portion thereof, and upon sensing an anomaly in a portion of the region, here, for example, a fungal disease infestation, automatically communicates an image illustrating the anomaly as well as the coordinates of the infested area, growth parameters and field parameters, preferably in real time or near real time.

In a preferred embodiment, the payload assembly 210 scans the entire field continuously, during both day and night, and employs different algorithms based on the operating parameters to sense anomalies. In one example, the payload assembly 210 compares the sensed thermal characteristics with historical information of average thermal measurement over time of different portions of the field, while taking into consideration growth parameters and field parameters.

Upon sensing an anomaly, as described above, the payload assembly 210 preferably communicates the information relating thereto, preferably via a wireless communication link, via any suitable medium, such as a line of sight, RF, satellite, internet or other link, to a computerized amelioration center 245, as described hereinbelow with reference to FIG. 6A, which may provide real time or near real time reports or amelioration, such as spraying. The communication may be via the cloud or a direct computer to computer or computer to human link. Alternatively, the communication to computerized amelioration center 245 may be via analysis engine 220.

Figure 6A:
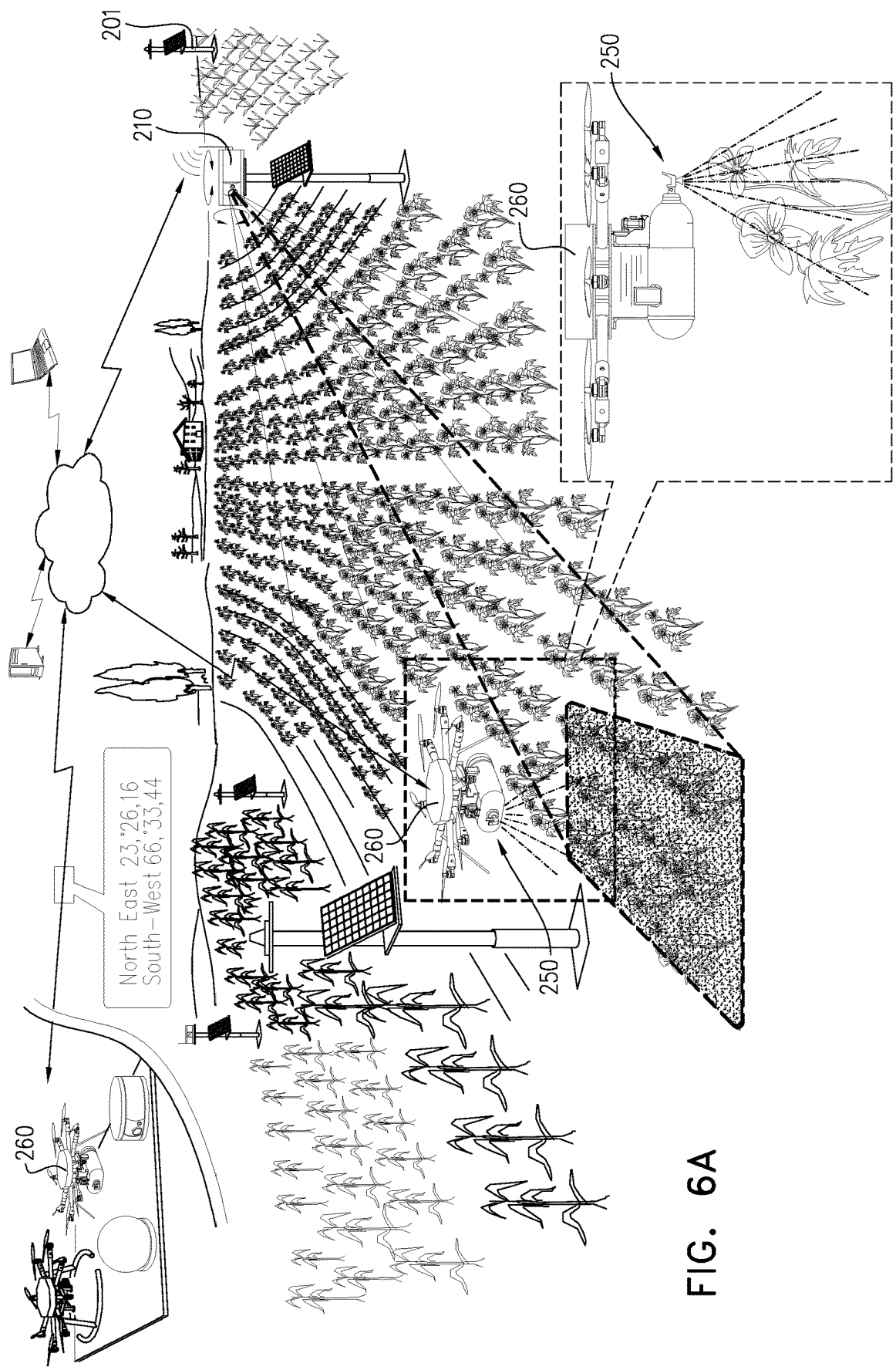
FIGS. 6A and 6B are simplified illustrations of respective automated and semi-automated plant growth amelioration provided by a system for monitoring plant growth of the type shown in any of FIGS. 3-5.

FIG. 6A shows an example of fully automatic amelioration, wherein the sensed anomaly is automatically ameliorated, as by spraying distressed plants at a location specified by the anomaly locator, using a drone-mounted computer controlled sprayer assembly 250 mounted on a drone 260.

Figure 6B:
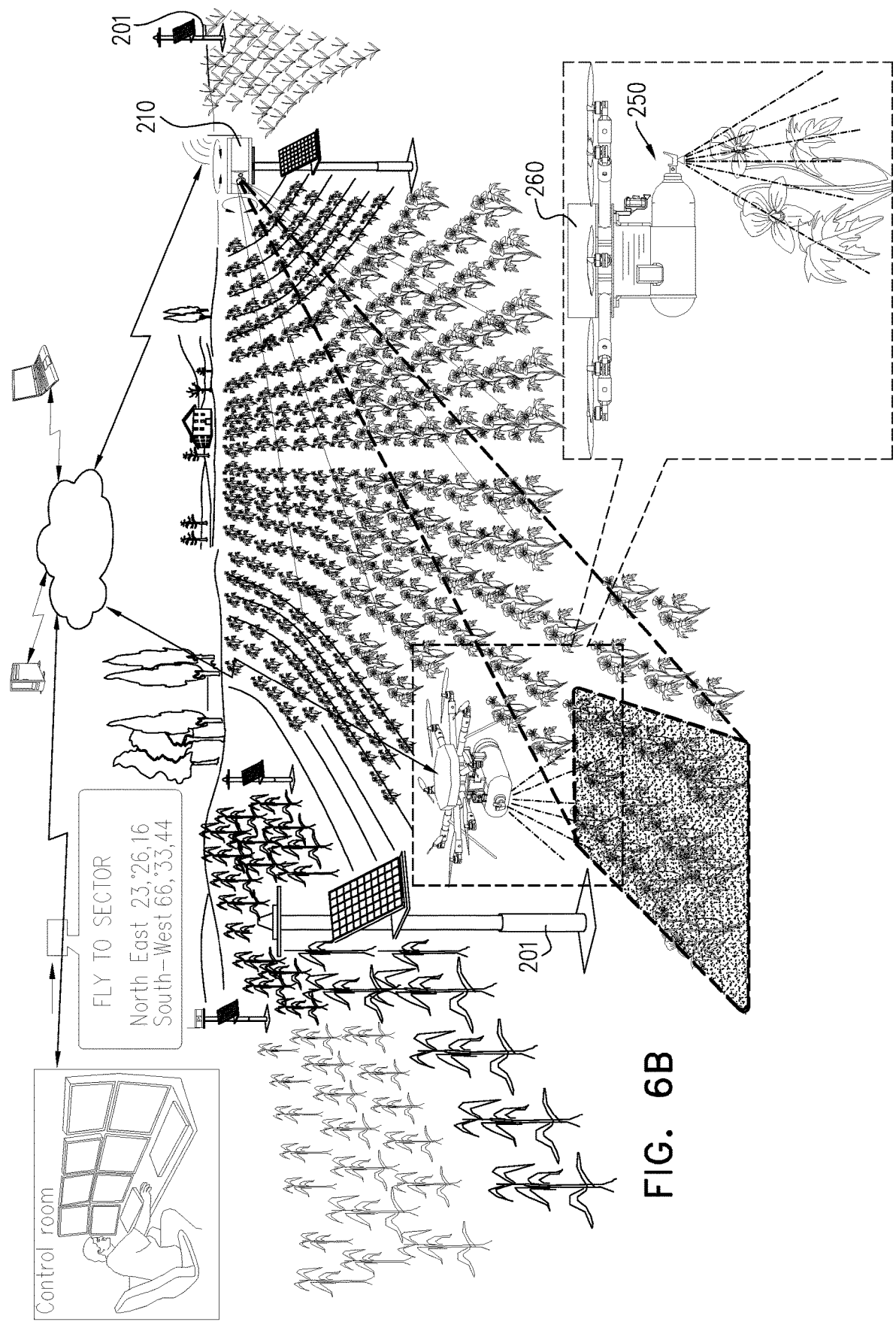

FIG. 6B illustrates partially automatic amelioration employing the system of FIGS. 2-5 which employs a human operator to control or approve the amelioration.

Figure 7:
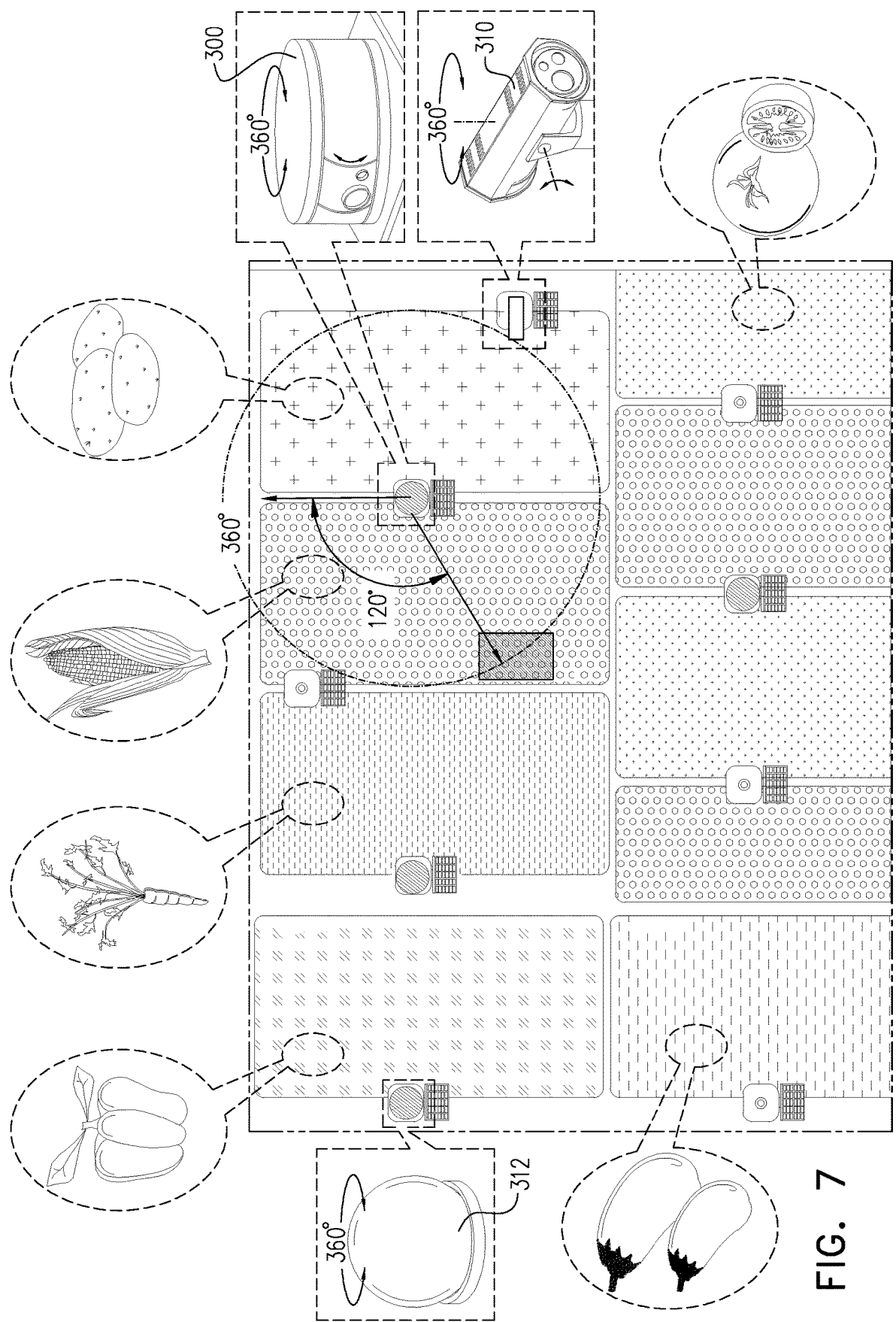
FIG. 7 is a simplified illustration of the operation of a system for monitoring plant growth of the type shown in any of FIGS. 2-6B with a variety of different crops.

Reference is now made to FIG. 7, which is a simplified illustration of the operation of a system for monitoring plant growth of the type shown in any of FIGS. 2-6B with a variety of different crops, such as peppers, carrots, corn and potatoes. It is seen that various types of sensors or payloads may be employed, such as a thermal sensor 300, a multi-spectral sensor 310 or a radar sensor 312. As indicated by arrows in FIG. 7, sensors may be operative to scan in a complete 360° rotation, either in a single continuous direction or in a back a forth direction, or in a back and forth direction covering any portion thereof, such as a 120° arc, as shown in the illustrated embodiment.

Figure 8:
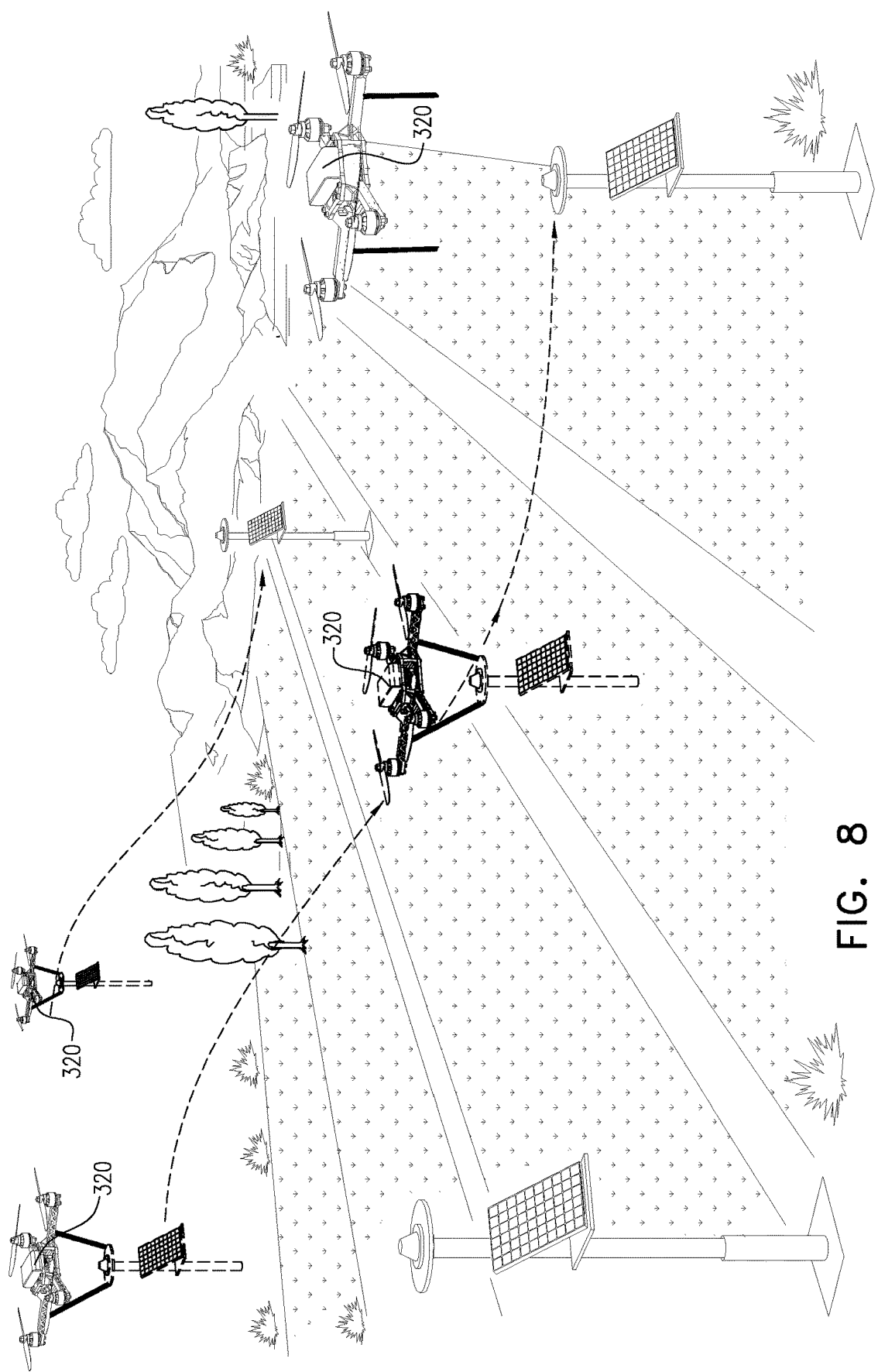
FIG. 8 is a simplified illustration of positioning and repositioning of elevated supports in a system for monitoring plant growth of the type shown in any of FIGS. 2-7.

Reference is now made to FIG. 8, which is a simplified illustration of positioning and repositioning of elevated supports in a system for monitoring plant growth of the type shown in any of FIGS. 2-7. It is appreciated that a drone 320, preferably having a high lifting capacity, may be employed for moving platforms 201 from place to place as needed at various stages of the growth of various crops in various seasons.

It will be appreciated by persons skilled in the art that the present invention is not limited by what has been shown and described hereinabove. Rather the present invention includes both combinations and subcombinations of various features described hereinabove and which are not in the prior art.

The invention claimed is:

1. A system for crop management comprising:
   a sensor which is located at a static location during measurement and is capable of sensing at least temperature characteristics of a multiplicity of plants in a field and having a resolution of individual plants or groups of plants, said sensor comprising a camera which is rotatably mounted on a generally vertical shaft, wherein said sensor is at least 6 meters above a canopy of said plants during said measurement; and
   a sensor output processor, receiving an output of said sensor and being operative to provide an output indication of a difference between a rate of change in at least temperature over time of a first specific plant or group of plants and a second specific plant or group of plants over a time interval of less than one day; and
   an amelioration sub-system, comprising:
      an anomaly locator indicating a location of at least one of said first specific plant or group of plants and said second specific plant or group of plants; and
      a drone-mounted computer controlled sprayer assembly, operative to spray distressed ones of said first specific plant or group of plants and said second specific plant or group of plants, thereby automatically ameliorating said difference between said rate of change in at least temperature over time.

2. The system for crop management according to claim 1 wherein said sensor output processor is operative to provide an output indication of a temperature difference between a temperature of said first specific plant or group of plants and said second specific plant or group of plants spatially adjacent thereto.

3. The system according to claim 2 comprising integrating functionalities for associating multiple said differences at multiple locations with a plant growth anomaly.

4. The system for crop management according to claim 1 wherein said output indication includes a spatial output location indication specifying the location of said first specific plant or group of plants.

5. The system for crop management according to claim 4 wherein said spatial output location is expressed in GIS coordinates.

6. The system according to claim 1 wherein said generally vertical shaft is a selectably raisable shaft which is mounted on a movable support, which normally does not move during operation of said sensor.

7. The system according to claim 1 comprising artificial intelligence analytics operative to ascertain from said output indication a probable cause of said difference.

8. The system according to claim 1 comprising artificial intelligence analytics operative to associate said difference with a plant growth anomaly.

9. The system according to claim 8 comprising recommendation functionality for recommending amelioration of said plant growth anomaly.

10. The system according to claim 1 wherein said sensor is at least 10 meters above said canopy of said plants during said measurement.

11. The system according to claim 1 wherein said sensor is at least 15 meters above said canopy of said plants during said measurement.

12. The system according to claim 1 wherein said sensor is at least 30 meters above said canopy of said plants during said measurement.

13. The system according to claim 1 wherein said multiplicity of plants is within a predetermined area of at least 10 hectares.

14. The system according to claim 1 wherein said multiplicity of plants is within a predetermined area of at least 50 hectares.

15. A system for crop management comprising:
    a sensor which is located at a static location during measurement and is capable of sensing at least temperature characteristics of a multiplicity of plants within a predetermined area of at least 10 hectares and having a resolution of individual plants or groups of plants, said sensor comprising a camera which is rotatably mounted on a generally vertical shaft; and
    a sensor output processor, receiving an output of said sensor and being operative to provide an output indication of a difference between a rate of change in at least temperature over time of a first specific plant or group of plants and a second specific plant or group of plants over a time interval of less than one day; and
    an amelioration sub-system, comprising:
       an anomaly locator indicating a location of at least one of said first specific plant or group of plants and said second specific plant or group of plants;
       a drone-mounted computer controlled sprayer assembly, operative to spray distressed ones of said first specific plant or group of plants and said second specific plant or group of plants, thereby automatically ameliorating said difference between said rate of change in at least temperature over time.

16. The system according to claim 15 wherein said predetermined area is at least 30 hectares.

17. The system according to claim 15 wherein said predetermined area is at least 50 hectares.

18. The system according to claim 15 wherein said sensor is at least 6 meters above a canopy of said plants during said measurement.

19. The system according to claim 15 wherein said sensor is at least 15 meters above a canopy of said plants during said measurement.

* * * * *